(12) United States Patent
Alizoti et al.

(10) Patent No.: US 12,329,901 B1
(45) Date of Patent: Jun. 17, 2025

(54) MEDICAMENT DELIVERY DEVICE WITH VIBRATING AIR FLOW

(71) Applicant: Trudell Medical International Inc., London (CA)

(72) Inventors: Neritan Alizoti, London (CA); George Baran, London (CA); Jason Suggett, London (CA)

(73) Assignee: Trudell Medical International Inc., London (CA)

( * ) Notice: Subject to any disclaimer, the term of this patent is extended or adjusted under 35 U.S.C. 154(b) by 719 days.

(21) Appl. No.: 17/118,163

(22) Filed: Dec. 10, 2020

Related U.S. Application Data

(60) Provisional application No. 62/947,965, filed on Dec. 13, 2019.

(51) Int. Cl.
*A61M 15/00* (2006.01)

(52) U.S. Cl.
CPC .... *A61M 15/0085* (2013.01); *A61M 15/0086* (2013.01); *A61M 15/009* (2013.01); *A61M 2205/3334* (2013.01); *A61M 2205/502* (2013.01); *A61M 2205/581* (2013.01); *A61M 2205/582* (2013.01); *A61M 2205/583* (2013.01); *A61M 2250/00* (2013.01)

(58) Field of Classification Search
CPC .......... A61M 15/0085; A61M 15/0086; A61M 15/009; A61M 2205/3334; A61M 2205/502; A61M 2205/581; A61M 2205/582; A61M 2205/583; A61M 2250/00; A61M 16/208; A61M 16/0006
See application file for complete search history.

(56) References Cited

U.S. PATENT DOCUMENTS

| | | | |
|---|---|---|---|
| 5,657,752 A | 8/1997 | Landis et al. |
| 5,972,327 A | 10/1999 | Lin et al. |
| 7,837,649 B1 | 11/2010 | Aboff |
| 8,389,529 B2 | 3/2013 | Moran et al. |
| 9,272,117 B2 | 3/2016 | Miledi |
| 9,375,540 B2 | 6/2016 | Pearson |
| 9,700,688 B2 | 7/2017 | Engelbreth et al. |
| 9,925,351 B2 | 3/2018 | Keener |
| 9,936,913 B2 | 4/2018 | Mills |
| 2006/0003030 A1 | 1/2006 | Chun-Ying et al. |
| 2009/0145434 A1 | 6/2009 | Herrmann |
| 2010/0024813 A1 | 2/2010 | Spector |

(Continued)

FOREIGN PATENT DOCUMENTS

| | | |
|---|---|---|
| BR | PI0806023 A2 | 8/2010 |
| CN | 1726961 A | 2/2006 |

(Continued)

OTHER PUBLICATIONS

Pederson et al. "Nasal Inhalation of Budesonide from Spacer in Children with Perennial Rhinitis and Asthma" Allergy, 1998, 6 pages.

*Primary Examiner* — Scott J Medway
*Assistant Examiner* — Anh Bui
(74) *Attorney, Agent, or Firm* — Crowell & Moring LLP (57) ABSTRACT

A medicament delivery device includes a chamber housing defining an interior volume, wherein the interior volume defines a medicament delivery flow path. A vibration inducing device communicates with the interior volume and is operable to introduce vibrations into the flow path.

23 Claims, 5 Drawing Sheets

(56) References Cited

U.S. PATENT DOCUMENTS

| | | |
|---|---|---|
| 2012/0108888 A1 | 5/2012 | Spector |
| 2014/0377389 A1 | 12/2014 | Budman et al. |
| 2015/0182766 A1 | 7/2015 | Dolezal et al. |
| 2016/0001035 A1 | 1/2016 | Keener |
| 2016/0058961 A1 | 3/2016 | Haas |
| 2016/0166847 A1 | 6/2016 | Choi et al. |
| 2017/0119986 A1 | 5/2017 | Poree |
| 2017/0182258 A1* | 6/2017 | Michael ............ A61M 5/31568 |
| 2018/0000696 A1 | 1/2018 | Villeneuve et al. |
| 2018/0221618 A1 | 8/2018 | Strauss et al. |
| 2018/0280638 A1* | 10/2018 | Buchmann ........... A61M 11/005 |
| 2019/0321570 A1* | 10/2019 | Rubin ................. A61M 16/209 |
| 2019/0336717 A1 | 11/2019 | Hickey et al. |
| 2019/0366018 A1* | 12/2019 | Conlon ............... A61M 15/009 |

FOREIGN PATENT DOCUMENTS

| | | |
|---|---|---|
| CN | 1927337 A | 3/2007 |
| CN | 101616708 B | 5/2013 |
| CN | 105943723 A | 8/2016 |
| DE | 4219535 A1 | 10/1992 |
| DE | 10 2004 038285 A1 | 4/2006 |
| EP | 0 986 413 B1 | 9/2004 |
| EP | 1 632 240 A1 | 3/2006 |
| EP | 1 201 258 B1 | 4/2009 |
| EP | 2 213 588 A1 | 8/2010 |
| EP | 2 042 209 B1 | 10/2013 |
| EP | 3 103 464 A1 | 12/2016 |
| EP | 3 178 525 A1 | 6/2017 |
| EP | 3 187 220 A1 | 7/2017 |
| EP | 3 360 477 A1 | 8/2018 |
| EP | 2 136 865 A2 | 9/2020 |
| JP | S6187621 A | 5/1986 |
| JP | H08-164207 A | 6/1996 |
| JP | 2706052 B2 | 1/1998 |
| JP | 5153948 B1 | 2/2013 |
| JP | 2013184949 A | 9/2013 |
| TW | I 300716 B | 9/2008 |
| WO | WO 03/075003 A1 | 9/2003 |
| WO | WO 2004026391 A1 | 4/2004 |
| WO | WO 2010/076904 A1 | 7/2010 |
| WO | WO 2013/132487 A1 | 9/2013 |
| WO | WO 2013133062 A1 | 9/2013 |
| WO | WO 2015/186124 A1 | 12/2015 |
| WO | WO 2017/119865 A1 | 7/2017 |
| WO | WO 2019/178693 A1 | 9/2019 |

\* cited by examiner

MEDICAMENT DELIVERY DEVICE WITH VIBRATING AIR FLOW

This application claims the benefit of U.S. Provisional Application 62/947,965, filed Dec. 13, 2019, entitled "Medicament Delivery Device With Vibrating Air Flow," the entire disclosure of which is hereby incorporated herein by reference.

TECHNICAL FIELD

The present invention relates generally to a medicament delivery device, such as a holding chamber, with a vibrating air flow, and also to medicament delivery assemblies and methods of delivering medicament or the like.

BACKGROUND

It is well known to deliver aerosolized medicaments to a patient via various devices, including nebulizers and aerosol dispensing devices, such as pressurized Metered Dose Inhalers (PMDI's) and valved holding chambers, in order to treat various conditions and diseases, including but not limited to various respiratory conditions and diseases such as asthma. In some embodiments, such devices may have dead space or other features that impede the mixing of a gas, such as air, and the medicament, disposed for example in an aerosol.

SUMMARY

Briefly stated, in one aspect, one embodiment of a medicament delivery device includes a chamber housing defining an interior volume, wherein the interior volume defines a medicament delivery flow path. A vibration inducing device communicates with the interior volume and is operable to introduce vibrations into the flow path.

In one embodiment, the chamber is configured as a valved holding chamber having an input end, an output end, and a one-way inhalation valve positioned at the output end. The flow path is defined between the input and output ends. In various embodiments, the vibration inducing device is disposed in the interior volume of the chamber housing. In various embodiments, the vibration inducing device may include one or more of a speaker, a rotating turbine, an oscillating piston or valve or a pea in a resonating chamber.

In another aspect, one embodiment of medicament delivery assembly includes the medicament delivery device and a drug delivery device coupled to the chamber housing, for example at the input end of a valved holding chamber in one embodiment.

In another aspect, one embodiment of a method of delivering a medicament includes introducing a medicament into the interior volume of the chamber housing, creating a flow through the interior volume of the chamber housing, inducing or introducing vibrations in the interior volume of the chamber housing with the vibration inducing device, and inhaling the medicament.

The various aspects and embodiments provide significant advantages over other medicament delivery assemblies and methods. For example and without limitation, a vibrating airflow increases the mixing of the air and aerosol, recirculates old/residual air from dead spaces, and improves the embedding of the drug onto the airway tissue. This is all made possible by the flow induced vibrations.

The present embodiments of the invention, together with further objects and advantages, will be best understood by reference to the following detailed description taken in conjunction with the accompanying drawings.

BRIEF DESCRIPTION OF THE DRAWINGS

FIG. 1 is a side perspective view of a first embodiment of a medicament delivery device.

FIG. 2 is a side perspective view of a second embodiment of a medicament delivery device.

FIG. 3 is a side perspective view of a third embodiment of a medicament delivery device.

FIG. 4 is a schematic showing the communication protocol between a user interface and a medicament delivery device.

FIG. 5A is a side perspective view of a fourth embodiment of a medicament delivery device.

FIG. 5B is an enlarged partial view of the vibration inducing device shown in FIG. 5A.

FIG. 6 is a side perspective view of a fifth embodiment of a medicament delivery device.

FIG. 7 is a side view of a sixth embodiment of a medicament delivery device.

FIG. 8 is a side view of the medicament delivery device shown in FIG. 7 being shaken by a user.

FIG. 9 is a side view of the medicament delivery device shown in FIG. 7 with a vibration inducing device producing a vibration.

FIG. 10 is a side view of the medicament delivery device shown in FIG. 7 with pMDI canister being actuated while the vibration inducing device is producing a vibration.

DETAILED DESCRIPTION OF THE PRESENTLY PREFERRED EMBODIMENTS

It should be understood that the term "plurality," as used herein, means two or more. The term "coupled" means connected to or engaged with, whether directly or indirectly, for example with an intervening member, and does not require the engagement to be fixed or permanent, although it may be fixed or permanent. It should be understood that the use of numerical terms "first," "second," "third," etc., as used herein does not refer to any particular sequence or order of components; for example "first" and "second" cavities may refer to any sequence of such features, and is not limited to the first and second cavities of a particular configuration unless otherwise specified. It should be understood that the terms "input end," "output end" and "inlet" refer to the function of those features during an inhalation phase, and that the inlet may serve the opposite function (removal or exit) during an exhalation phase. The phrase "fluid communication" refers to the ability of a fluid, whether a gas or liquid, to flow or pass from one component or feature to another component or feature, including intermittently, for example when a valve is open to permit such flow. The phrase "communicate" refers to the ability of a feature or component to transmit or have an effect on another feature or component, whether by direct contact, for example by fluid communication, or by indirect contact, for example by vibration, and includes wireless communication, for example Bluetooth. The phrase "ambient environment" is the environment or atmosphere, e.g. air, surrounding the component or feature, including for example the mask. As used herein, the term "upstream" refers to the direction from which a flow of gas is originating while the term "downstream" refers to the direction toward which the flow is traveling, for example during inhalation, air flows from an upstream medicament delivery device to a downstream user.

The term "fluid" may include one or both of a gas and/or liquid. The term "gas" includes but is not limited to air.

Figure 4:
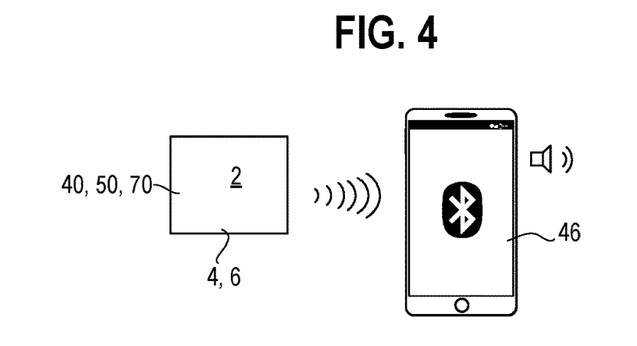
Figure 5A:
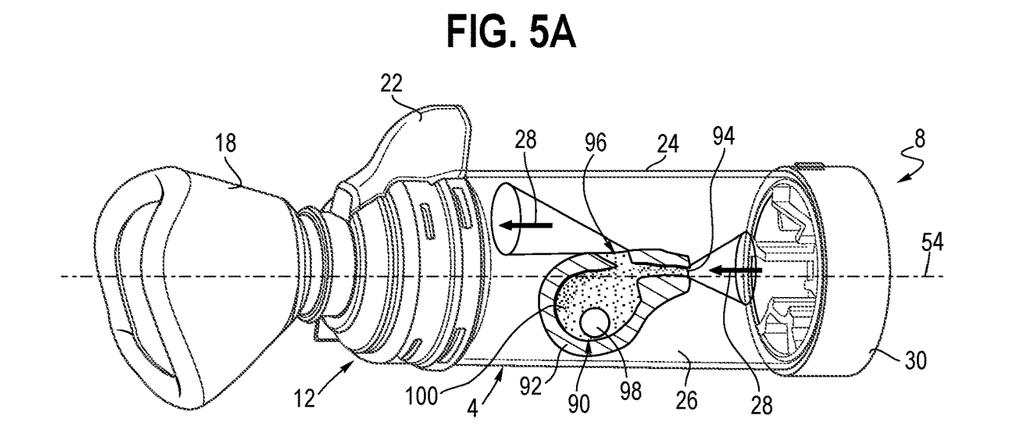
Figure 5B:
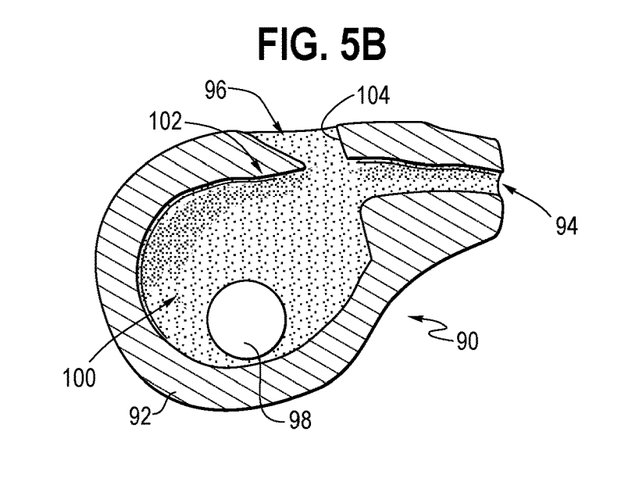

Referring to FIGS. 1-10, various medicament delivery assemblies 2 are shown as including a medicament delivery device, configured for example as a holding chamber 4 in one embodiment. The medicament delivery device may alternatively be configured as a nebulizer 6 as schematically illustrated in FIG. 4. The holding chamber may have various antistatic properties. The holding chamber has an input end 8 configured to mate with a drug delivery device 10, such as a pressurized metered dose inhaler pMDI. The holding chamber further includes an output end 12 configured with a baffle and a one-way inhalation valve 16 in one embodiment. The output end 12 may further include an annular flange or tube, configured as a mouthpiece in one embodiment, which is shaped to engage and support a user interface 18. The holding chamber may be configured with a visual indicator 22 that provides visual indicia when the user is exhaling and/or inhaling. Various suitable holding chambers are disclosed in U.S. Pat. Nos. 6,336,453, 7,360,537, 6,904,908, the entire disclosures of which are hereby incorporated herein by reference.

The holding chamber includes a chamber housing 24 that has a generally cylindrical cross-sectional shape that defines an interior volume 26 of space for receipt therein of aerosolized medication from the drug delivery deice 10, e.g. the pMDI. A front end of the chamber housing includes a dome-shaped head piece that includes a central circular opening that is in fluid communication with the interior volume of space of the chamber housing. The opening defines the periphery of a flow path as it exits the opening. A flow path 28 is defined between the input and output ends.

Figure 2:
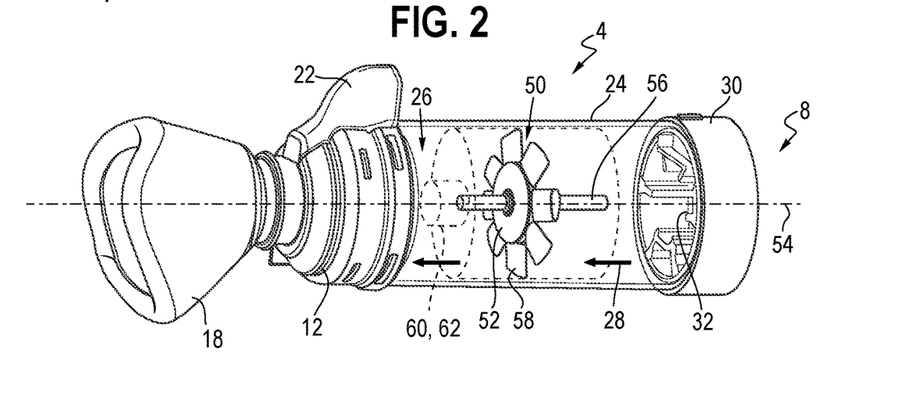
Figure 3:
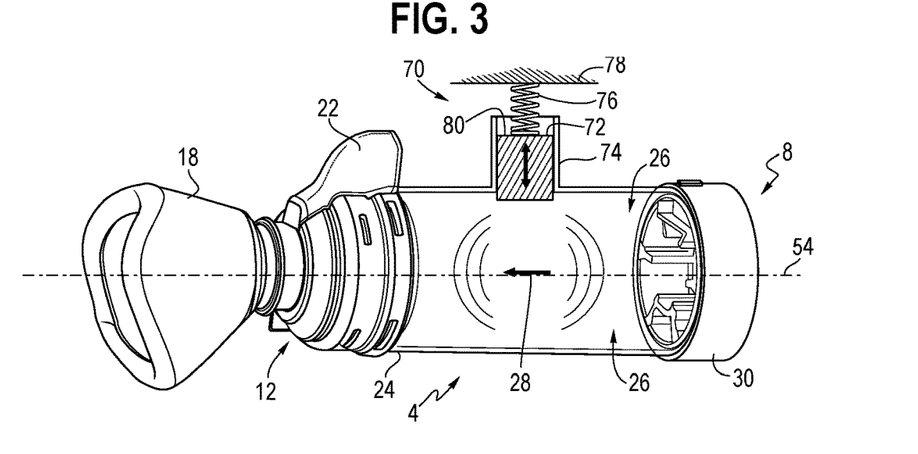

The rear, input end 8 of the chamber housing includes a detachable and flexible backpiece 30 having an opening 32 suited to receive a mouthpiece portion 34 of a receptacle or actuator boot 36 that houses a pMDI canister 38 as shown in FIG. 2. It should be understood that the same drug delivery device 10 may be coupled to the medicament delivery devices, and in particular the holding chamber 4, shown in FIGS. 2, 3 and 5A. Examples of possible pMDI adapters and canisters to be used in conjunction with the holding chamber are also described in U.S. Pat. Nos. 5,012,803, 5,012,804, 5,848,588 and 6,293,279, the entire contents and disclosures of which are hereby incorporated herein by reference.

When a force is applied to a stem of the pMDI canister 38, a portion of the substance is discharged from the discharge end of the pMDI receptacle in aerosol form into the interior volume 26 of the chamber housing 24. The aerosol medication particles within the chamber housing are withdrawn therefrom by having the patient inhale through the user interface 18, which may be configured for example as a mouthpiece or mask.

The pMDI canister 38 contains a substance, preferably a drug or medication suspension or solution under pressure. In one embodiment, the substance dispensed is an HFA propelled medication suspension or solution formulation. Other propellants, such as CFC may also be used. It should be pointed out that while the described embodiments regard an aerosol delivery system for the delivery of an aerosolized medication from a pMDI, other aerosol delivery systems are contemplated that can be used within the spirit of the present invention. For example, it is contemplated that the vibration inducing device may be incorporated with an aerosol delivery system such as existing ventilator systems, dry powder inhalers and nebulizers, in a manner similar to that described below Examples of nebulizers that can be adapted to include a vibration inducing device are disclosed in U.S. Pat. Nos. 5,823,179 and 6,044,841, the entire contents of which are incorporated herein by reference.

The present invention is not limited to the treatment of human patients. For example, it is contemplated that the medicament delivery devices may be used for administering a drug or medication to animals, including for example and without limitation equines, cats, dogs, etc. An example of an equine mask used in combination with such medicament delivery devices is disclosed in U.S. Pat. No. 5,954,049, the entire contents of which are incorporated herein by reference.

The holding chamber 4 may further include an input end that is suitable for connection to a ventilator circuit or other oxygen supply. Such holding chambers are further described and disclosed in U.S. Publication No. 2010/0101570 and U.S. Pat. No. 8,151,794, the entire disclosures of which are hereby incorporated herein by reference.

Referring to FIGS. 1-3, 5A and 10, vibrating airflow increases the mixing of the aerosol and/drug with the air, recirculates old air from dead spaces, and helps with better drug embedding onto the airway tissue. In various embodiments, the frequency range of these vibrations is in the range of between and including 5 to 35 Hz.

Referring to FIG. 1, a first embodiment of a medicament delivery device includes a vibration inducing device 40 communicating with the interior volume 26 of the chamber housing. The vibration inducing device is operable to introduce vibrations into the flow path. In one embodiment, the vibration inducing device 40 includes a speaker 42 communicating with the interior volume. In one embodiment, the speaker is disposed in the interior volume, and has an output end 44 directed toward the output end 12 of the holding chamber 4. The speaker may be a wireless speaker/Bluetooth/Ant+/BLE. The wireless speaker 42 may be controlled by a user interface 46, for example a mobile device such as a smart phone or tablet, with a smart application as shown in FIG. 4. In one mode of operation, the speaker 42 receives an input from the user interface 46 and is operable to output or push bass frequencies that create flow induced vibrations in the flow path 28.

In a second embodiment, shown in FIG. 2, the vibration inducing device 50 includes a rotating turbine 52 communicating with the interior volume. In one embodiment, the rotating turbine is disposed in the interior volume and rotates on a shaft 56 about a central, longitudinal axis 54. The rotating turbine includes a plurality of blades 58 that create a vibration in the interior volume 26. In one embodiment, a motor 60 is connected to the rotating turbine. The motor is connected to, or includes, a power source 62 and is operable to rotate the turbine 52 about the axis 54 in response to an input from the motor 60. The motor 60 may include a switch or other control system, which may be actuated wirelessly via Bluetooth by the user interface 46. The device may include an accelerometer and a controller, such as a microcontroller, as described below with respect to the embodiment of FIG. 6, with the accelerometer sensing when the holding chamber 4 is picked up for use and turns the device on, with the controller providing an input to the motor. In an alternative embodiment, the rotating turbine 52 is self-powered, and is rotatable in response to a gas flow in the flow path 28 of the interior volume, without input from a motor, produced for example by an inhalation flow during inspiration by the user. In other embodiments, the rotating turbine 52 may be operable both with and without input from the motor.

In a third embodiment, shown in FIG. 3, the vibration inducing device 70 includes an oscillating piston 72 communicating with the interior volume. For example, a cavity or cylinder 74 may open into the side of the chamber housing 24 and communicate with the interior volume 26. The piston 72 is moveably disposed in the cylinder 74 and reciprocally slides or translates along the sides thereof. A spring 76 or other actuator is connected between a ground 78, or base, which may be incorporated into the holding chamber 4, and an end of the piston 80. The piston 72 oscillates back and forth in the cylinder, thereby creating pressure variation and pulsations that induce oscillations in the flow path 28 in the interior volume 26 of the chamber housing 24. The piston may be configured alternatively as a diaphragm, which vibrates or oscillates in response to a pulsating pressure, or as a valve that produces a pulsing vibration. The oscillating piston 72 is operable at a frequency in a range of greater than or equal to 5 Hz and less than and equal to 35 Hz.

Induced oscillations are produced when the piston 72 or valve moves back and forth in the cylinder 74 to create pressure variation/pulsations, inducing vibratory oscillations to the drug delivery inhalation flow path 28. An electromagnetic driver may be coupled to the piston to oscillate the piston at a predetermined and desired frequency. For example, the piston or valve may be driven by an electromagnet similar to an audio speaker, or by a connected smart application algorithm through the user interface 46. As shown in the embodiment of FIG. 3, the piston 72 is not disposed in the interior volume 26 and does not interfere with the flow path 28. The piston 72 or valve may include a switch or other control system, which may be actuated wirelessly via Bluetooth by the user interface 46. The device may include an accelerometer and a controller, such as a microcontroller, as described below with respect to the embodiment of FIG. 6, with the accelerometer sensing when the holding chamber 4 is picked up for use and turns the device on, with the controller providing an input to the piston or valve.

Referring to FIG. 4, any of the various embodiments of the vibration inducing device 40, 50, 70, 130, 170 disclosed herein may be wirelessly connected to the user interface 46. The user interface is operable to provide audio, visual and/or haptic feedback to user. For example, a smart application interface may show and control the oscillations frequency on a screen of the user interface 46 and communicate with the user via audio, visual, or haptic feedback by guiding them throughout the therapy session administered by the medicament delivery device.

Referring to FIGS. 5A and B, the vibration inducing device 90 includes a resonating chamber 92 having an inlet 94, defining a windway, and an outlet 96 communicating with the interior volume 26 of the chamber housing. In one embodiment, the resonating chamber is disposed in the interior volume 26 of the chamber housing, with the inlet 94 facing upstream toward the input end 8 and the outlet facing orthogonal and/or downstream relative to the longitudinal axis 54 and/or toward the output end 23. The vibration inducing device may be position in the interior volume such that the inlet 94 is substantially aligned with the axis 44. A small, relatively light ball, referred to as a pea 98, is disposed in an interior volume 100 of the resonating chamber 92. The pea 98 is sized such that it may not pass through the inlet 94 or outlet 96 of the resonating chamber, but rather is trapped within the interior volume 100, albeit moveable therein. The outlet 96 has an edge 102 that is spaced apart from the junction between the inlet 94 and interior volume 100, and is substantially aligned with an upper surface of the inlet passageway such that the edge 102 diverts flow from the inlet 94 into the interior volume 100 of the resonating chamber, whereinafter the flow disturbs and moves the pea 98 about within the interior volume 100 of the resonating chamber 92 and thereby creating vibrations. In this way, the pea 98 is moveable within the resonating chamber 92 in response to a flow in the flow path 28 between the input and output ends 8, 12 of the holding chamber. The edge 102 is adjacent to, and forms part of the outlet. Across from the edge is a surface 104 that defines a portion of the outlet and diverts air flow exiting the resonating chamber and functions as a sound reflector and airflow converter that directs the flow and vibrations exiting the resonating chamber into the interior volume 26 of the chamber housing in a downstream direction toward the output end 12 as shown in FIG. 5A. The vibration inducing device defines or produces a whistle, with the pea 98 rattling around inside the resonating chamber 92 and creating a chaotic vibrato effect that pulsates sound and produces vibrations within the chamber housing 24.

Referring to FIG. 6, the vibration inducing device 130 includes a vibratory device, such as a tuning fork, bell, vibrating reed or quartz tuning fork. The tuning fork, shown in FIG. 6, is an acoustic resonator having a pair of prongs, or tines 132, forming a U-shaped bar of elastic metal (e.g., steel). The device includes an accelerometer 136 and a controller 134, such as a microcontroller. The accelerometer may sense when the holding chamber 4 is picked up for use and turns the device on. The system also includes a flow sensor 138 and/or microphone 140 disposed in the interior volume 26 of the holding chamber. The flow sensor may include any type of sensor suitable for detecting a flow, including for example and without limitation, pressure and/or force sensors, light transmission sensors, light reflectance, a strain gauge, a Hall Effect element, humidity and/or temperature sensors, a Venturi tube, a restrictive orifice, a pitot static tube, one or more strain/flex sensors, a capacitance sensor, a reed switch, one or more vibration/acceleration sensors, combinations thereof, etc. For example, the microphone may serve as a flow sensor, detecting noise from the flow inside the chamber. The system further includes an actuator 142, for example a liner actuator, which may be actuated by the controller to quickly extend (and retract) a thrust pin or ram 144 to impact or ding the tuning fork, e.g., by engaging one of the tines 132, causing the tuning fork to vibrate inside the interior chamber. When the holding chamber 4 is put down, or remains at rest for a predetermined period of time (e.g., 20-60 seconds), the system will go to sleep. The linear actuator may include a switch or other control system, which may be actuated wirelessly via Bluetooth by the user interface 46.

In another embodiment of a medicament delivery device shown in FIGS. 7-10, a vibration inducing device 170 includes an oscillating mass 184 supported on a cantilever spring 176 in the interior volume 26 of the holding chamber 4. The cantilever spring 176 has a first end 178 coupled to an interior of the chamber housing. In one embodiment, the spring 176 extends forwardly in a cantilever fashion from a support 188 in a longitudinal direction 174, with a second (free) end 180 positioned adjacent a passage opening 172 upstream of the inhalation valve 16. It should be understood that the spring may be oriented in other directions. A valve 190, configured as a thin plate or diaphragm in one embodiment, is connected to, or extends transversely from, the second end 180 of the spring 176. The valve/plate is disposed adjacent to and over the passage opening 172, and is spaced slightly apart therefrom, such that the valve/plate does not close the passage opening 172 when in an at-rest position. It should be understood that the passage opening may be omitted on one embodiment, with the plate/valve 190 disposed adjacent a baffle at the outlet opening of the holding chamber, or alternatively, the baffle may be omitted with the passage defining the passage opening 172. In operation, the user shakes the medicament delivery device such that the mass 184, cantilever spring 176 and valve/plate 190 oscillates back and forth (i.e., up and down) in the interior volume 26 of the cylinder relative to the passage opening 172, thereby creating pressure variation and pulsations that induce oscillations in the flow path 28 in the interior volume 26 of the chamber housing 24. The oscillating mass 184 spring and plate/valve 190 are operable at a frequency in a range of greater than or equal to 5 Hz and less than and equal to 35 Hz.

Figure 7:
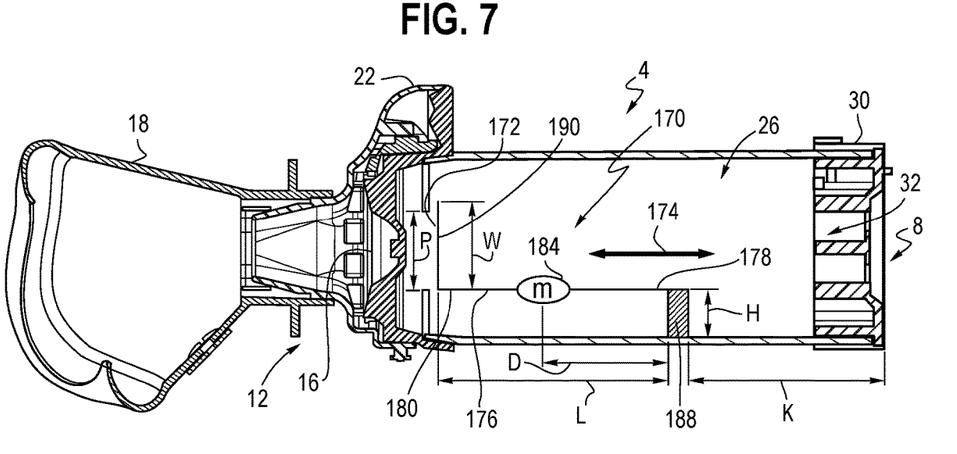

Referring to FIGS. 7, in one embodiment, the passage opening 172 has a diameter P equal to or between 5 and 40 mm, while the plate/valve has a diameter W equal to or between 5 and 45 mm. As shown in FIGS. 7-10, the free end of the plate/valve distal from the second end 180 extends slightly upward, or beyond the top of the passage opening 172 in the at-rest position, such that the plate/valve 109 engages the edge of the opening 172 as the spring bends or is displaced downwardly. The length L of the spring 176 is equal to or between 0 and 90 mm. The mass 184 is disposed on, or coupled to the spring 176, at an intermediate location between the first and second ends 178, 180, for example at a midpoint thereof, or at a distance D from the first end 178 equal to or between 5 and 90 mm and a distance K from the end of the device equal to or between 0 and 90 mm. In one embodiment, the spring 176 is spaced apart from an interior surface 200 of the interior space of the holding chamber 4 a distance H equal to or between 2 and 40 mm, such that the spring may bend and oscillate up and down in the interior space 26 of the holding chamber 4. In one embodiment, the mass (m) is equal to or between 0.01 and 25 g. The valve/plate 190 may be made of silicone, TPE or other suitable materials. The spring 176 may be may made of stainless steel, copper alloy, plastic, or other suitable materials. In one embodiment, the spring 176 and valve 190 are integrally formed from the same material. The mass 184 may be made of plastic, metal, or other suitable materials.

Induced oscillations are produced when the mass 184, spring 176 and plate/valve 190 moves back and forth in the interior chamber adjacent and relative to the passage opening 172 to create pressure variation/pulsations, inducing vibratory oscillations to the drug delivery inhalation flow path 28, both upstream in the interior volume 26 and downstream in the output end 12 and user interface 18. In an alternative embodiment, an electromagnetic driver may be coupled to the spring to oscillate the mass, spring and plate/valve at a predetermined and desired frequency. For example, the mass, spring and/or valve may be driven by an electromagnet similar to an audio speaker, or by a connected smart application algorithm through the user interface 46. The mass 184 or valve may include a switch or other control system, which may be actuated wirelessly via Bluetooth by the user interface 46. The device may include an accelerometer and a controller, such as a microcontroller, as described below with respect to the embodiment of FIG. 6, with the accelerometer sensing when the holding chamber 4 is picked up for use and turns the device on, with the controller providing an input to the mass or valve.

Figure 1:
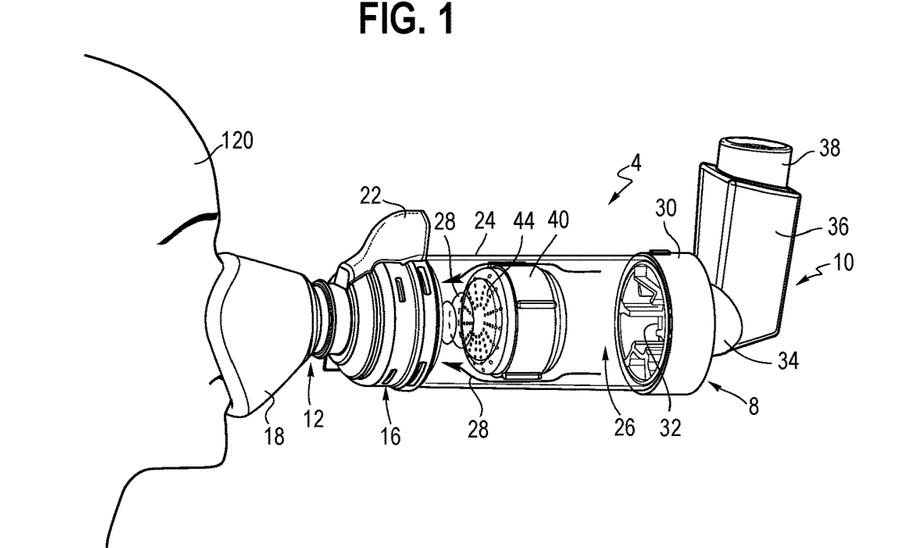

In operation, the medicament delivery device is positioned such that the patient 120 is engaged with the user interface 18, for example with the mask or mouthpiece, which may be configured as a nasal mask that surrounds or overlies the nasal passageways of the user, as shown in FIG. 1. It should be understood that the patient would similarly interface with the medicament delivery devices shown in FIGS. 2, 3, 5A and 6. The inhalable substance, such as an aerosolized medicament, may be dispensed by actuating the pressurized metered dose inhaler 10. For example, the container 38 of the pMDI may be reciprocally moved relative to the actuator boot 36 so as to release a metered dose of aerosolized medicament through the mouthpiece 34 coupled to the input end 8 of the holding chamber 4. The medicament is introduce or drawn into the interior volume 26 of the chamber housing 24, thereby creating a flow through the interior volume of the chamber housing along flow path 28. At the same time, the operation includes inducing vibrations in the interior volume 26 of the chamber housing with one or more of the vibration inducing devices 40, 50, 70, 90, 130. The vibrations may be induced by the flow in the flow path 28 actuating the vibration inducing devices, or with the vibration inducing devices being independently actuated, for example by way of an auxiliary motor, linear actuator 142, electromagnetic actuator or pulsating pressure source, any and all of which may be coordinated with the inspiratory flow created by the user's inhalation.

Figure 6:
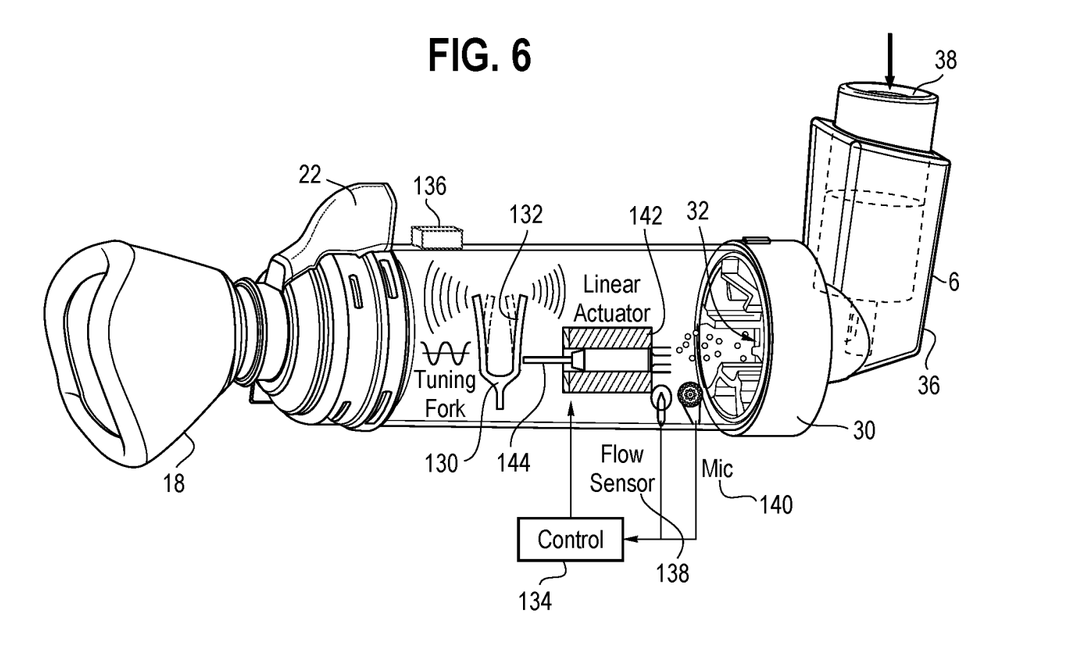

For example, with respect to the embodiment of FIG. 6, the flow sensor 138 may detect a flow during inspiration, with the flow sensor providing an input signal to the controller 134. At the same time, or separately, the microphone 140 may pick up the actuation, for example the noise from actuation of the pMDI and/or the flow of gases in the chamber, and provide an input signal to the controller 134. The controller 134, in turn, provides an output signal, which serves as an input signal for the linear actuator 142, causing the actuator to quickly extend (and retract) the push pin 144 and thereby contact or ding at least one of the tines 132 of the tuning fork 130, causing the tines 132 to resonate or vibrate.

Figure 8:
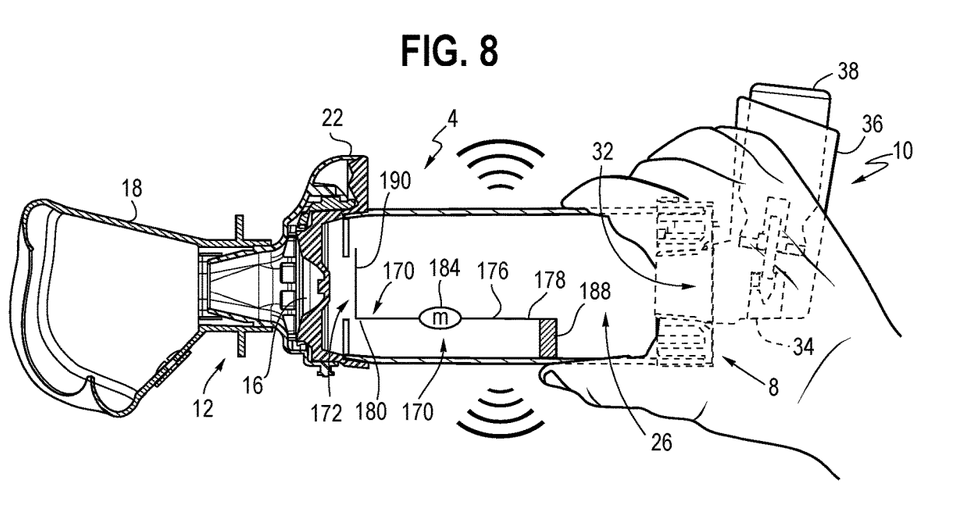
Figure 9:
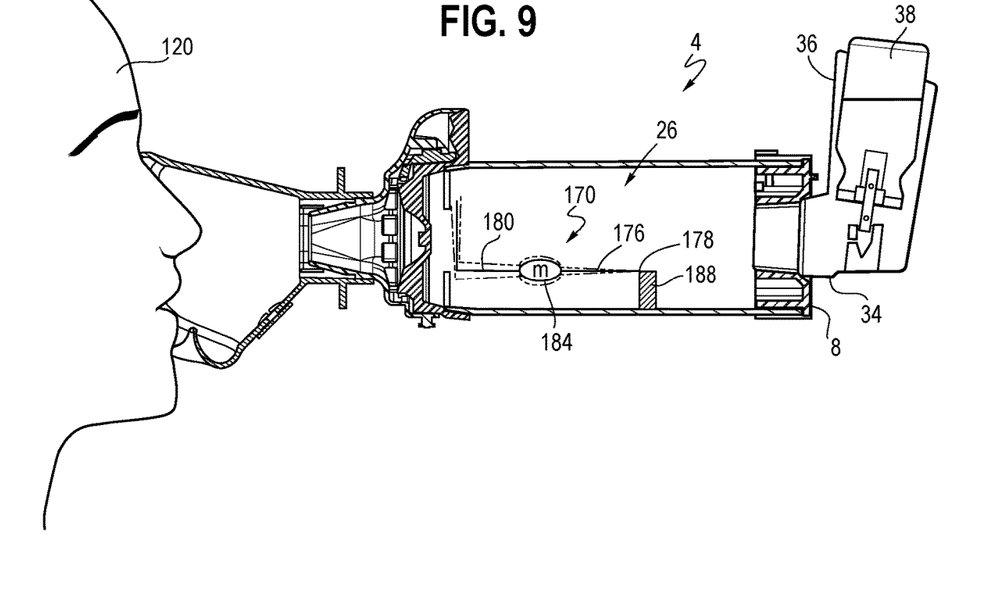
Figure 10:
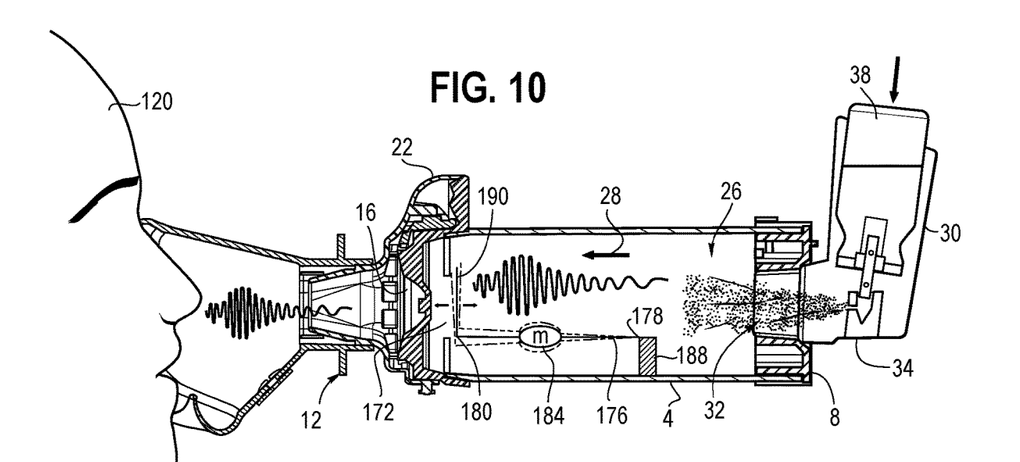

In the embodiment of FIGS. 7-10, the user grasps the medicament delivery device and shakes the device to initiate a vibration of the mass 184 spring 176 and valve 190 within the interior volume 26, as shown in FIG. 8. Thereafter, the device is positioned such that the patient 120 is engaged with the user interface 18, for example with the mask or mouthpiece, which may be configured as a nasal mask that surrounds or overlies the nasal passageways of the user, as shown in FIG. 9, with the mass 184, spring 174 and plate/valve 190 still vibrating or oscillating. The inhalable substance, such as an aerosolized medicament, may be dispensed by actuating the pressurized metered dose inhaler 10, as shown in FIG. 10, while the mass, spring and plate/valve are oscillating relative to the passage opening 172. For example, the container 38 of the pMDI may be reciprocally moved relative to the actuator boot 36 so as to release a metered dose of aerosolized medicament through the mouthpiece 34 coupled to the input end 8 of the holding chamber 4. The medicament is introduce or drawn into the interior volume 26 of the chamber housing 24, thereby creating a flow through the interior volume of the chamber housing along flow path 28. At the same time, the operation includes inducing vibrations in the interior volume 26 of the chamber housing with the vibration inducing devices 170. The vibrations may be induced by the flow in the flow path 28 actuating the vibration inducing devices, or with the vibration inducing devices being independently actuated, for example by way of shaking as previously described, or by way of an auxiliary motor, linear actuator 142, electromagnetic actuator or pulsating pressure source, any and all of which may be coordinated with the inspiratory flow created by the user's inhalation.

The vibrations and vibrating air flow, created by any of the above-noted embodiments, increase the mixing of the air and aerosol, and assist in recirculating old/residual air retained in the interior volume 26, for example in any dead spaces. As such, the vibrations and vibrating air flow lead to increased drug delivery to the airway tissue. The device may be actuated one or more times as needed and prescribed. The medicament or other inhalable substance, such as oxygen, may be administered by a metered dose inhaler or nebulizer, and may be positioned in a ventilator circuit, or other system providing an oxygen supply.

In various embodiments, the inhalable substance is an aerosolized medication that may be administered using the medicament delivery assembly and device, which medication may include, without limitation, corticosteroids, such as beclamethasone, budesonide, flunisolide, cilcesonide, and fluticasone, and bronchodilators, such as albuterol, proventil, levalbuterol, salmeterol and pirbuterol.

Although the present invention has been described with reference to preferred embodiments, those skilled in the art will recognize that changes may be made in form and detail without departing from the spirit and scope of the invention. As such, it is intended that the foregoing detailed description be regarded as illustrative rather than limiting and that it is the appended claims, including all equivalents thereof, which are intended to define the scope of the invention.

What is claimed is:

1. A medicament delivery device comprising:

a chamber housing defining an interior volume, wherein the interior volume defines a medicament delivery flow path; and a vibration inducing device disposed in and communicating with the interior volume, wherein the vibration inducing device is operable to introduce vibrations into the medicament delivery flow path, wherein the vibration inducing device is configured to induce vibrations in the medicament delivery flow path in response to an inhalation flow along the medicament delivery flow path actuating the vibration inducting device.

2. The medicament delivery device of claim 1 wherein the chamber housing comprises a holding chamber having an input end, an output end, and a one-way inhalation valve positioned at the output end, wherein the medicament delivery flow path is defined between the input and output ends.

3. The medicament delivery device of claim 2 wherein the vibration inducing device comprises a rotating turbine communicating with the interior volume.

4. The medicament delivery device of claim 3 wherein the rotating turbine is rotatable in response to a gas flow in the flow channel.

5. The medicament delivery device of claim 2 wherein the vibration inducing device comprises a vibratory device communicating with the interior volume.

6. The medicament delivery device of claim 5 wherein the vibratory device comprises a tuning fork.

7. The medicament delivery device of claim 6 further comprising an actuator engagable with the tuning fork.

8. The medicament delivery device of claim 7 wherein the actuator comprises a moveable pin.

9. The medicament delivery device of claim 7 further comprising a sensor operably connected to a controller, wherein the controller provides an input to the actuator.

10. The medicament delivery device of claim 9 wherein the sensor comprises at least one of a flow pressure sensor and/or a microphone.

11. The medicament delivery device of claim 1 wherein the vibration inducing device is wirelessly connected to a user interface.

12. The medicament delivery device of claim 11 wherein the user interface is operable to provide audio, visual and/or haptic feedback to user.

13. The medicament delivery device of claim 2 wherein the vibration inducing device comprises a resonating chamber having an inlet and an outlet communicating with the interior volume of the chamber housing, and a pea disposed in the resonating chamber, wherein the pea is moveable within the resonating chamber in response to a flow between the input and output.

14. The medicament delivery device of claim 13 further comprising an edge spaced apart from the inlet adjacent the outlet.

15. The medicament delivery device of claim 13 wherein the outlet comprises a sound reflector and/or airflow converter directed to the output end.

16. The medicament delivery device of claim 13 wherein the inlet faces the input end of the first chamber.

17. The medicament delivery device of claim 1 wherein the vibration inducing device comprises a cantilever spring and a mass coupled to the spring.

18. A medicament delivery device comprising:

a chamber housing defining an interior volume, wherein the interior volume defines a medicament delivery flow path, and wherein the chamber housing comprises a passage opening defining in part the medicament delivery flow path; and a vibration inducing device communicating with the interior volume, wherein the vibration inducing device is operable to introduce vibrations into the flow path, wherein the vibration inducing device comprises a cantilever spring and a mass coupled to the spring, and wherein the vibration inducing device further comprises a valve connected to the cantilever spring, wherein the valve is disposed adjacent the passage opening and is moveable relative to the passage opening.

19. A medicament delivery assembly comprising the medicament delivery device of claim 2 and a drug delivery device coupled to the input end.

20. A method of delivering a medicament comprising:

providing a medicament delivery device of claim 2;

introducing a medicament into the interior volume of the chamber housing;

creating a flow through the interior volume of the chamber housing;

inducing vibrations in the interior volume of the chamber housing with the vibration inducing device; and inhaling the medicament.

21. The method of claim 20 wherein the inducing vibrations is initiated prior to the introducing the medicament into the interior volume.

22. The method of claim 20 wherein inducing the vibrations in the interior volume comprises inducing the vibrations with the vibration inducing device in response to the flow through the interior volume.

23. The medicament delivery device of claim 1, wherein the vibration inducing device is configured to induce vibrations in the medicament delivery flow path in response to shaking the chamber housing.

* * * * *

UNITED STATES PATENT AND TRADEMARK OFFICE
CERTIFICATE OF CORRECTION

PATENT NO. : 12,329,901 B1
APPLICATION NO. : 17/118163
DATED : June 17, 2025
INVENTOR(S) : Neritan Alizoti, George Baran and Jason Suggett Page 1 of 1

It is certified that error appears in the above-identified patent and that said Letters Patent is hereby corrected as shown below:

In the Claims

In Column 9, Line 43, delete "inducting" and replace with --inducing--

Signed and Sealed this
Thirtieth Day of September, 2025

John A. Squires
*Director of the United States Patent and Trademark Office*